United States Patent
Griebling et al.

(10) Patent No.: US 12,303,408 B2
(45) Date of Patent: May 20, 2025

(54) POWERED FINGER WITH LOCKING RACK MECHANISM

(71) Applicant: RCM Enterprise L.L.C., Olympia, WA (US)

(72) Inventors: Erich Theodore Griebling, Olympia, WA (US); Catherine Rocille Treadwell, Olympia, WA (US)

(73) Assignee: RCM Enterprise L.L.C., Olympia, WA (US)

( * ) Notice: Subject to any disclaimer, the term of this patent is extended or adjusted under 35 U.S.C. 154(b) by 113 days.

(21) Appl. No.: 17/316,357

(22) Filed: May 10, 2021

(65) Prior Publication Data

US 2021/0361445 A1   Nov. 25, 2021

Related U.S. Application Data

(60) Provisional application No. 63/027,259, filed on May 19, 2020.

(51) Int. Cl.
*A61F 2/58* (2006.01)
*A61F 2/50* (2006.01)
(Continued)

(52) U.S. Cl.
CPC ............... *A61F 2/586* (2013.01); *A61F 2/70* (2013.01); *A61F 2002/5083* (2013.01);
(Continued)

(58) Field of Classification Search
CPC .... A61F 2/586; A61F 2/70; A61F 2002/5083; A61F 2002/6836; A61F 2002/6854; A61F 2002/701; A61F 2002/704; B25J 15/0009
See application file for complete search history.

(56) References Cited

U.S. PATENT DOCUMENTS

| 1,277,747 | A | | 9/1918 | O'Connor |
| 1,484,913 | A | * | 2/1924 | Surry ..................... A61F 2/583 |
| | | | | 623/57 |

(Continued)

FOREIGN PATENT DOCUMENTS

| CN | 204274728 U | 4/2015 |
| CN | 106038009 B | 2/2018 |

(Continued)

OTHER PUBLICATIONS

International Search Report and Written Opinion dated Sep. 10, 2021 for International Application No. PCT/US2021/031637, 12 pages.

(Continued)

*Primary Examiner* — Jerrah Edwards
*Assistant Examiner* — Maximilian Tobias Spencer
(74) *Attorney, Agent, or Firm* — Perkins Coie LLP (57) ABSTRACT

This disclosure provides systems, apparatuses, and devices for a powered prosthetic digit. The disclosed devices restore prehension in a person with missing fingers or thumb by providing motor-driven extension and flexion, and opposition to forces in the extension direction via a pawl and locking rack ratchet mechanism, thereby allowing an individual to manipulate or stabilize objects. In one embodiment, a digit comprises a base configured to be removably couplable to an anchor, a first segment pivotably coupled to the base, and a second segment removably coupled to the first segment. The first segment comprises a rack with a plurality of rack teeth and a pawl with a nose configured to engage with the rack to prevent pivoting of the first segment in a rotational direction corresponding to extension of the prosthetic digit. The second segment comprises a drive gear operable to pivot the first segment with respect to the base.

20 Claims, 9 Drawing Sheets

(51) Int. Cl.
*A61F 2/68* (2006.01)
*A61F 2/70* (2006.01)
(52) U.S. Cl.
CPC .......... *A61F 2002/6836* (2013.01); *A61F 2002/6854* (2013.01); *A61F 2002/701* (2013.01); *A61F 2002/704* (2013.01)

(56) References Cited

U.S. PATENT DOCUMENTS

| | | | |
|---|---|---|---|
| 2,425,154 | A | 8/1947 | Hibbard |
| 2,493,776 | A | 1/1950 | Alberto et al. |
| 4,685,926 | A * | 8/1987 | Haupt ............... A61F 2/64 623/43 |
| 4,685,929 | A | 8/1987 | Monestier |
| 5,800,571 | A | 9/1998 | Carlson et al. |
| 5,888,246 | A * | 3/1999 | Gow ............... A61F 2/583 623/64 |
| 5,941,914 | A | 8/1999 | Jacobsen et al. |
| 6,361,570 | B1 | 3/2002 | Gow |
| 9,592,134 | B2 | 3/2017 | Varley |
| 9,913,737 | B2 | 3/2018 | Hunter |
| 9,999,522 | B2 | 6/2018 | Gill |
| 10,653,539 | B2 | 5/2020 | Cazenave |
| 10,869,773 | B2 | 12/2020 | Martinez-luna et al. |
| 10,905,570 | B2 | 2/2021 | Segil et al. |
| 11,083,600 | B2 | 8/2021 | Gill |
| 11,229,533 | B2 | 1/2022 | Segil et al. |
| 11,554,029 | B2 | 1/2023 | Griebling et al. |
| 2005/0021154 | A1 | 1/2005 | Brimalm |
| 2006/0212129 | A1* | 9/2006 | Lake ............... A61F 2/70 623/64 |
| 2009/0096746 | A1 | 4/2009 | Kruse et al. |
| 2012/0109337 | A1* | 5/2012 | Schulz ............... A61F 2/586 623/64 |
| 2012/0303136 | A1 | 11/2012 | Macduff |
| 2012/0308806 | A1 | 12/2012 | Leto et al. |
| 2013/0041476 | A1 | 2/2013 | Schulz |
| 2013/0127791 | A1 | 5/2013 | Siuta |
| 2014/0107805 | A1 | 4/2014 | Varley |
| 2014/0303750 | A1 | 10/2014 | Macduff |
| 2015/0190245 | A1 | 7/2015 | McLeary et al. |
| 2015/0230941 | A1 | 8/2015 | Jury |
| 2016/0015100 | A1 | 1/2016 | Leto |
| 2016/0224138 | A1 | 8/2016 | Adkins |
| 2016/0367383 | A1 | 12/2016 | Sensinger et al. |
| 2017/0007424 | A1 | 1/2017 | Gill |
| 2017/0020691 | A1 | 1/2017 | Thompson et al. |
| 2017/0056208 | A1 | 3/2017 | Thompson et al. |
| 2018/0036145 | A1* | 2/2018 | Jury ............... A61L 27/165 |
| 2018/0064563 | A1 | 3/2018 | Gill |
| 2018/0110631 | A1 | 4/2018 | Cazenave |
| 2018/0235293 | A1 | 8/2018 | Lee et al. |
| 2018/0296369 | A1 | 10/2018 | Smit et al. |
| 2019/0328550 | A1* | 10/2019 | Akhtar ............... A61F 2/5044 |
| 2019/0374353 | A1 | 12/2019 | Schulz |
| 2020/0054464 | A1 | 2/2020 | Sensinger et al. |
| 2020/0060361 | A1 | 2/2020 | Depriest et al. |
| 2021/0085490 | A1 | 3/2021 | Griebling et al. |
| 2021/0293643 | A1* | 9/2021 | Correll ............... A61F 2/54 |
| 2021/0361445 | A1 | 11/2021 | Griebling et al. |
| 2022/0133509 | A1 | 5/2022 | Segil et al. |
| 2022/0313456 | A1 | 10/2022 | Acevedo et al. |
| 2023/0320873 | A1 | 10/2023 | Griebling et al. |
| 2024/0390164 | A1 | 11/2024 | Griebling et al. |

FOREIGN PATENT DOCUMENTS

| | | | | |
|---|---|---|---|---|
| CN | 109381285 | A | 2/2019 | |
| DE | 2329929 | A1 | 1/1975 | |
| DE | 102017005761 | B4 | 2/2020 | |
| EP | 3110372 | B1 | 1/2018 | |
| EP | 3842015 | A2 | 6/2021 | |
| EP | 3856088 | B1 | 8/2022 | |
| FR | 2277569 | A2 | 2/1976 | |
| GB | 145267 | A | 7/1920 | |
| JP | 2015146998 | A | 8/2015 | |
| WO | 2010018358 | A2 | 2/2010 | |
| WO | 2016187133 | A1 | 11/2016 | |
| WO | WO-2017061879 | A1 * | 4/2017 | ............ A61F 2/583 |
| WO | 2021061681 | A1 | 4/2021 | |
| WO | 2021236370 | A1 | 11/2021 | |
| WO | 2022211824 | A1 | 10/2022 | |
| WO | 2023080796 | A1 | 5/2023 | |

OTHER PUBLICATIONS

ISA, International Search Report, PCT Application No. PCT/2020/052066, mailed Dec. 10, 2020, 9 pages.
Segil, Jacob L. et al. "The Point Digit: Mechanical Design and Testing of a Ratcheting Prosthetic Finger," Abstract, 41st Annual Meeting of the American Society of Biomechanics, Boulder CO, Aug. 8-11, 2017, 2 pages.
Ventimiglia, Paul. Major Qualifying Project submitted to Faculty of Worcester Polytechnic Institute, "Design of a Human Hand Prosthesis," Apr. 26, 2012, 75 pages.
European Application No. 20869041.2 Extended Supplementary Search Report and Opinion Mailed Sep. 8, 2023, pp. 1-6.
Japanese Application No. 2022-517781 Office Action Mailed May 20, 2024, pp. 1-6.
U.S. Appl. No. 17/346,126 Final Office Action mailed Aug. 5, 2024, pp. 1-28.
U.S. Appl. No. 17/346,126, Non-Final Office Action Mailed Jan. 9, 2024, pp. 1-25.
U.S. Appl. No. 18/078,693 Final Office Action Mailed Sep. 16, 2024, pp. 1-8.
U.S. Appl. No. 18/078,693, Non-Final Office Action Mailed Mar. 26, 2024, pp. 1-6.
Kickler, Nils, European Application No. 21809498.5 Extended European Search Report Mailed May 31, 2024, pp. 1-10.
International Search Report and Written Opinion from International Application No. PCT/US2021/026909, dated Jul. 21, 2021.
International Search Report from PCT Application No. PCT/US2024/031109, dated Aug. 23, 2024.
U.S. Appl. No. 17/316,357, Non-Final Office Action Mailed Jun. 23, 2022.
U.S. Appl. No. 17/221,722, Notice of Allowance Mailed Dec. 4, 2024.
U.S. Appl. No. 17/221,722, Non-Final Office Action Mailed Jan. 19, 2024.
U.S. Appl. No. 17/221,722, Final Office Action Mailed Oct. 20, 2023.
U.S. Appl. No. 17/221,722, Non-Final Office Action Mailed Apr. 12, 2023.
Extended European Search Report from European Application No. 21935405, dated Jan. 15, 2025.

* cited by examiner

POWERED FINGER WITH LOCKING RACK MECHANISM

CROSS REFERENCE TO RELATED APPLICATION

This application claims priority to U.S. Provisional Patent Application No. 63/027,259, filed May 19, 2020, which is hereby incorporated by reference in its entirety.

TECHNICAL FIELD

The present technology generally relates to an electronic prosthesis to replace finger(s) or a thumb in partial or full hand loss conditions.

BACKGROUND

Partial hand loss is the most common upper extremity amputation and has historically been underserved by conventional treatment. Most partial hand amputations are traumatic in origin, and many amputations occur in workplaces where manual labor is performed. Partial hand loss alters the ability to sort mail, play an instrument, return to a vocation, or even dress oneself and cut or hold food. The injury is so devastating that manual laborers are often unable to return to the same line of work.

The primary goal of functional partial or full hand prosthetic intervention is to restore opposition grasp: a sufficiently forceful grasp between the thumb and the fingers such that objects can be stabilized and manipulated. Conventional technology, however, has struggled to provide restorative interventions because of the wide range of anatomical and functional presentations post-amputation, and the complexity of replacing a powerful, dexterous, and small portion of the human hand. Partial hand loss includes any amputation distal to or through the carpal bones, including finger loss. Within this definition, four distinct zones can be considered: (1) distal to the metacarpophalangeal joint (MCP, or "knuckle"); (2) at or proximal to the MCP joint, but distal to the carpal bones (transmetacarpal); (3) at the carpal bones; and (4) thenar (full or partial thumb).

Available prosthetic interventions for transmetacarpal partial hand amputees can be broadly divided into three categories: (1) cosmetic restoration; (2) passive prostheses; and (3) driven (active) prostheses. Cosmetic restoration describes a realistic silicone restoration meant to resemble the original anatomy, which almost exclusively provide psychosocial support for the individual, with very little functional capability. While invaluable in the rehabilitation process, cosmetic restorations are often abandoned within a few years.

Passive prostheses are devices that are not actively driven. In recent years, the passive category has expanded to include adjustable locking systems. These devices typically replace digits and have one, two, or three joints mimicking the MCP, proximal interphalangeal (PIP), and distal interphalangeal (DIP) joints. They are spring loaded and adjustable to several postures representing different angles of digit orientation. Due to their robust nature and simplicity, passive prostheses are often the most utilized choice for return to work in manual labor environments.

Active prostheses can be powered by the body or by electricity. Body-powered devices are operated by a more proximal intact joint via linkages, cables, or straps. Some systems use cables routed across the wrist joint to actuate artificial fingers in response to wrist flexion. Another exemplary partial hand system uses a shoulder harness to drive fingers or a thumb in an open/close fashion. These systems, however, suffer from low output force at the hand.

BRIEF DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

DETAILED DESCRIPTION

A. Overview

The present technology is directed to an electronic prosthetic finger (hereafter "digit") configured to replace a finger or thumb in partial or full hand loss conditions. The digit may be controllable by a user-generated signal and may be capable of relatively quick movement, but is generally not configured for applying substantial active gripping force. Once the locking mechanism is engaged, the digit is configured to passively resist relatively large forces via: (1) a disengagement of the geared power drivetrain (e.g., by a spring); and (2) corresponding engagement of a rack and pawl mechanism that resists motion in the extension direction. The power drivetrain may be substantially unloaded upon opposition such that grasping and object manipulation can be performed with limited work and without passive resistance provided by the powertrain. As a result of disengagement of the drivetrain and engagement of a locking mechanism, a relatively small battery is capable of powering the digit. As such, the battery may be sized and configured to be integrated onboard the digit, or can be mounted external to the digit. In embodiments where the battery is onboard the digit, the battery and other electronics of the digit may be encapsulated for water resistance.

Modern electric partial hand prostheses in the current technology generally include individually motorized fingers reliant on a battery pack and user generated signals (e.g., inertial, external to body, myoelectric, joint position, and/or direct to muscle bundle, among others) to determine hand grasp patterns. Grasping is achieved by either the active torque capability of the digit (closing force applied during entire grasping function), or by passive locking of a non-reverse-drive gear train (such as a worm gear and worm pair). Size restrictions for direct current (DC) motors and gear trains configured to fit into a mechanism envelope the size of a finger phalanx cause current technology prostheses to make a restrictive compromise between closing force capability and finger speed—two primary performance metrics of a powered prosthetic digit. The torque limit ratings of small motors and gear train components require a substantial gear-down ratio to increase the active and passive grasping force to functional levels. The required gear-down ratio leads to systems operating well below the average anatomic task-oriented metacarpophalangeal (MCP) joint grasp speed (e.g., about 186 deg/sec.). In some current technologies, the average multiarticulating system prosthetic finger MCP joint speed is about 80 deg/sec, and the average force output at the fingertip is about 9.3 N. Additionally, the use of non-backdriveable gear pairs introduces significant inefficiencies to drivetrains in systems where battery weight is already cumbersome.

Electronic prosthetic systems for partial hand amputees in the current technology were adapted from designs for full hand replacement. Applying full hand solutions to partial hand presentations disregards the configuration of partial hand amputees with at least a thumb or finger intact, and leaves in place an unnecessary compromise between speed and force. If an intact digit is present, the concept of "synergetic prehension" becomes relevant to the prosthetic digit. Synergetic prehension describes the observation that relatively low work is performed during the act of grasping: the excursion of fingers as they approach an object usually occurs with low resistance, and when an object is grasped, force increases but excursion is minimal. Embodiments of the present technology can incorporate one or more aspects of synergetic prehension by providing relatively fast and weak power drivetrains in combination with a passively engaged ratchet locking mechanism. In this way, when an intact finger or thumb (or a high-powered prosthetic digit) applies a large force against an object, the powered digits of the present technology need only move quickly into position and then passively resist the large force. This configuration allows relatively small motors and small, highly efficient drivetrains to move the digit into position. The low work requirement of the powered digit decreases the required battery capacity, minimizing the size of power supplies. As a result of this optimization, the motor, battery, and other controls may be mounted within the digit itself, rather than remotely. These integrated configurations eliminate the need for power to cross the wrist and other joints, and makes a removable and rechargeable independent finger module possible. In other embodiments, one or more of the components of the powered digit may be mounted remote to the digit.

In some embodiments of the present technology, the digit is configured to have flexion (e.g., grasp movement) at speeds of greater than 140 deg/sec at the MCP joint, provide less than 2 N of active force, have a power output at the tip of the digit of less than 200 mW, and resist extension forces (e.g., the weight of a grasped object) of greater than 222 N. In one example, the power output at the tip of the digit can be calculated using the angular velocity at a joint (e.g., the MCP or PIP joint) and the maximum static force at the tip of the digit (e.g., using a load cell or a scale with the force vector in the normal direction). In other examples, the power output at the tip of the digit can be calculated using any suitable method.

Digits configured in accordance with the present technology may be capable of relatively quick flexion during use (e.g., grasping) to more closely mimic the movement of an intact human hand. The resistance of extension forces counteracts the force applied by an intact opposable finger or thumb (or a high-powered prosthetic finger or thumb) during grasping. In some partial hand amputees, one or more fingers may remain intact, and the prosthetic digit can be configured to resist relatively large loads with flexion speed that approaches or matches the typical task-oriented movement of the intact finger(s).

Digit motion and grasp configuration may be controlled via a number of user generated signals such as EMG, potentiometers, cables, goniometers, switches, IMUs, accelerometers, etc. These signals may be transmitted by wired or wireless transmission and may originate at any point on the body of the user or remote to the body of the user. The signals may be used alone or in combination with other signals and may create simple motions or multiple types of motions and grasps, depending on the control scheme. In some embodiments, the digit is controlled with wireless signals via wrist motion. As such, a sensor may be applied across the wrist joint to capture posture in both flexion/extension and radial/ulnar deviation (RUD). The posture creates angular data signals in the sensor that are transmitted to the digits and used to control individual digit posture and/or velocity, or relative digit posture and/or velocity when multiple prosthetic digits are in use. In other embodiments, the digit motion is controlled via an algorithm, function, or command (e.g., voice command, software command, etc.).

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the claims, but are not described in detail with respect to FIGS. 1A-6B.

Reference throughout this specification to "one embodiment" or "an embodiment" means that a particular feature, structure or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

B. Selected Embodiments of Prosthetic Digits

Figure 1A:
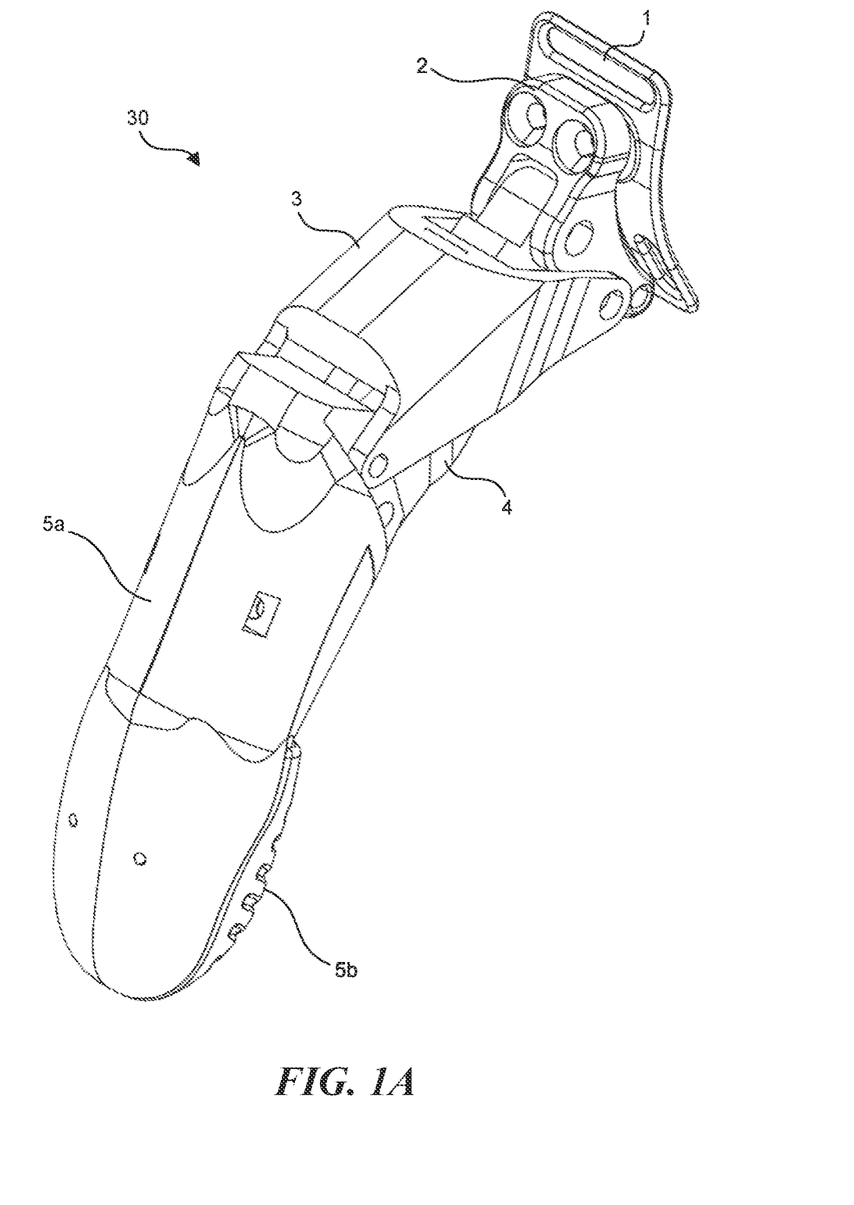
FIGS. 1A and 1B show perspective and elevation views, respectively, of a powered prosthetic digit with a locking rack mechanism configured in accordance with an embodiment of the present technology.
Figure 1B:
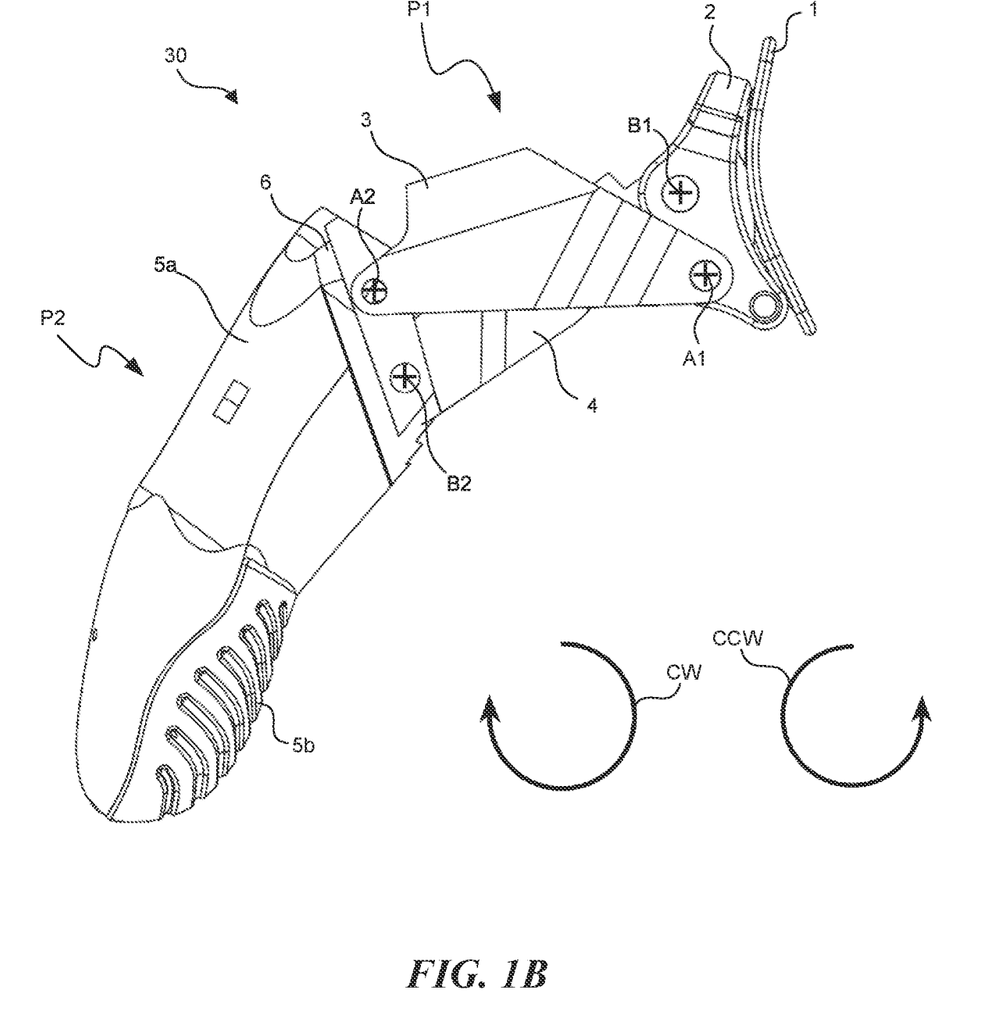

FIGS. 1A and 1B show perspective and elevation views, respectively, of a powered two-segment prosthetic digit 30 configured in accordance with an embodiment of the present technology. The digit 30 may be mounted to a rigid or flexible substrate for use by the user (not shown), which can include a socket (e.g., a partial hand socket, transradial socket, etc.) or frame. The substrate secures the digit 30 to the hand of the user in the approximate position of the anatomic digits of the user. In some embodiments, it is possible to mount the system in a fashion that is non-anatomic, such as in the case of unique clinical presentations. The digit 30 generally includes an anchor piece 1 configured to be affixed to or embedded in the socket of the user (not shown) and a base piece 2 attached to the anchor piece 1 via fasteners or any other suitable attachment method. The digit 30 can be detached from the hand of the user without disturbing the anchor piece 1 by removing the base piece 2 from the anchor piece 1.

As best seen in FIG. 1B, the two-segment digit includes first and second segments P1 and P2, generally representing bones of the finger, with the first segment P1 (e.g., a proximal or base segment) generally corresponding to the proximal phalanx, and the second segment P2 (e.g., a distal segment) generally corresponding to the middle and distal phalanx together, with the joint therebetween generally representing the PIP joint.

Referring again to FIGS. 1A and 1B together, the anchor piece 1 may be configured to be attached to or embedded in the stump interface of the user (see, e.g., representations of the stump interface in FIGS. 6A and 6B), and may include features designed to allow for successful integration with a fabricated socket. The materials can be temperature resistant to withstand the exothermic epoxy reactions expected in socket fabrication. The anchor piece 1 may also include various slots, holes, and other attachment features intended to allow for successful integration with carbon fiber, epoxy, silicone, and other anchoring methods typically used in the prosthetics field. In some embodiments, the anchor piece 1 and base piece 2 may be configured such that only one attachment orientation between the components is possible, e.g., to ensure proper installation fitment by the user. In other embodiments, however, the components may have various possible attachment orientations.

In the embodiment illustrated in FIGS. 1A and 1B, the second segment P2 may include a cosmetic and grip fairing 5a having a grip portion 5b with materials configured to increase the friction of the grip fairing 5a and the grip portion 5b. The grip fairing 5a may be mounted to the first segment P1 by a fastener or other suitable feature, e.g., a press fit, snap-to-fit, mechanical lock, button lock, twist lock, threads, detent lock, interference lock, etc. The grip fairing 5a and grip portion 5b may provide a silicone interface with objects for improved grip and allow the user to select designs and colors, or to replace these cosmetic pieces when wear occurs and/or when the battery needs replacement, etc., without needing to replace the second segment P2.

Referring to FIG. 1B, the digit 30 may include a pair of crossed linkages—a first linkage 3 and a second linkage 4—each rotatably pinned to the base piece 2 at first and second offset rotational joints A1 and B1, respectively. The distal ends of the first and second linkages 3 and 4 are rotatably pinned to a connector plate 6 at third and fourth offset rotational joints A2 and B2, respectively. The first and second linkages 3 and 4, together with the base piece 2 and the connector plate 6, form a coupled proximal crossed four-bar linkage to interact with the second segment P2 and provide a relatively smooth motion and kinematic space for the digit 30 similar to a portion of an anatomic finger. As will be explained in greater detail below, rotation of the first and second linkages 3 and 4 about the first and second offset rotational joints A1 and B1 will cause increased rotation of the connector plate 6 in the same direction, and thereby rotation of the second segment P2.

The proximal four-bar linkage transitions the digit 30 through a range of motion from full extension toward full flexion (flexion movement). During use of the digit 30 in the full extension position, e.g., when gripping an object, the first and second linkages 3 and 4 rotate counterclockwise (direction CCW in FIG. 1B) about the rotational joints A1 and B1. During such counterclockwise rotation, the third offset rotational joint A2 moves in a counterclockwise orbital path relative to the first offset rotational joint A1, and the fourth offset rotational joint B2 moves in a counterclockwise orbital path relative to the second offset rotational joint B1. The geometry of the first and second linkages 3 and 4, and the relatively fixed position of the base piece 2, causes orbital movements of the connector plate 6 with respect to the base piece 2 and a rotational tilt of the connector plate 6 in the counterclockwise direction at a greater angular velocity than the rotation of the first and second linkages 3 and 4 with respect to the base portion 2. In this regard, flexion of the digit 30 causes relative rotation between the first and second segments P1 and P2, with P2 rotating faster than P1 with respect to the base portion 2, similar to the natural articulation of the PIP joint. During motion from full flexion toward full extension (extension movement), the components rotate clockwise (direction CW in FIG. 1B) about the rotational joints A1 and B1, opposite to the motion described above. This motion may occur when the user wants to release grip on an object and/or to reset the position of the digit 30 to grasp another object.

Figure 2:
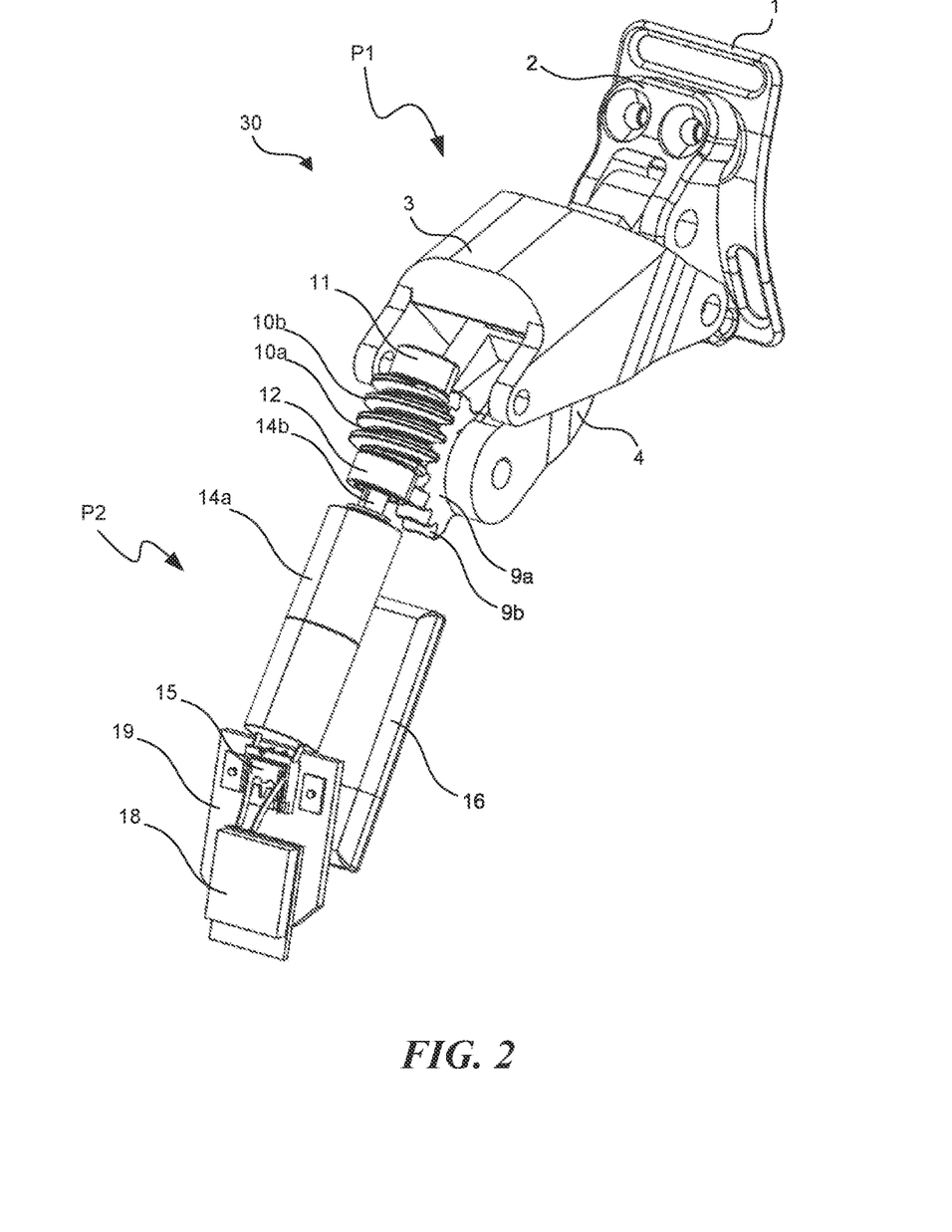
FIG. 2 shows a perspective view of the powered prosthetic digit of FIGS. 1A and 1B with the fairings removed.

FIG. 2 shows a perspective view of the digit 30 with the grip fairing 5a and grip portion 5b (FIG. 1B) removed for sake of clarity. The second segment P2 of the digit 30 may include various components internal to the grip fairing 5a (FIG. 1B), including a drive gear (e.g., a worm screw 10a) having worm teeth 10b configured to engage with a positioning gear 9a having positioning teeth 9b. The worm screw 10a may be rotatable within first and second bearings 11 and 12. The worm screw 10a may be positioned inline with a motor shaft 14b of a DC motor 14a. The motor 14a may be electrically coupled to a connector 15 on an electronics control board 19 having a microprocessor 18. The motor 14a may be powered by a battery 16 electrically coupled to a connector 17 (see FIG. 3) on the electronics control board 19. The electronics control board 19 may further include various components to operate the digit, such as a wireless receiver, a motor controller, a position sensor, etc., which have not been shown in the Figures for sake of clarity. The electronics control board 19 may also contain a port for charging, inductive charging coils, or the like. In various embodiments, all of the electronics may be potted to provide a high level of moisture resistance and/or a waterproof designation. In other embodiments, the battery is positioned external to the digit 30 (e.g., on the arm of the user) and provides power to the motor remotely. Digits configured in accordance with the present technology may be used in combination with a prosthetic digit at the thumb position configured with a high-strength motor (which will generally be slower in articulation angular speed, but may have increased gripping strength compared to faster digits).

Figure 3:
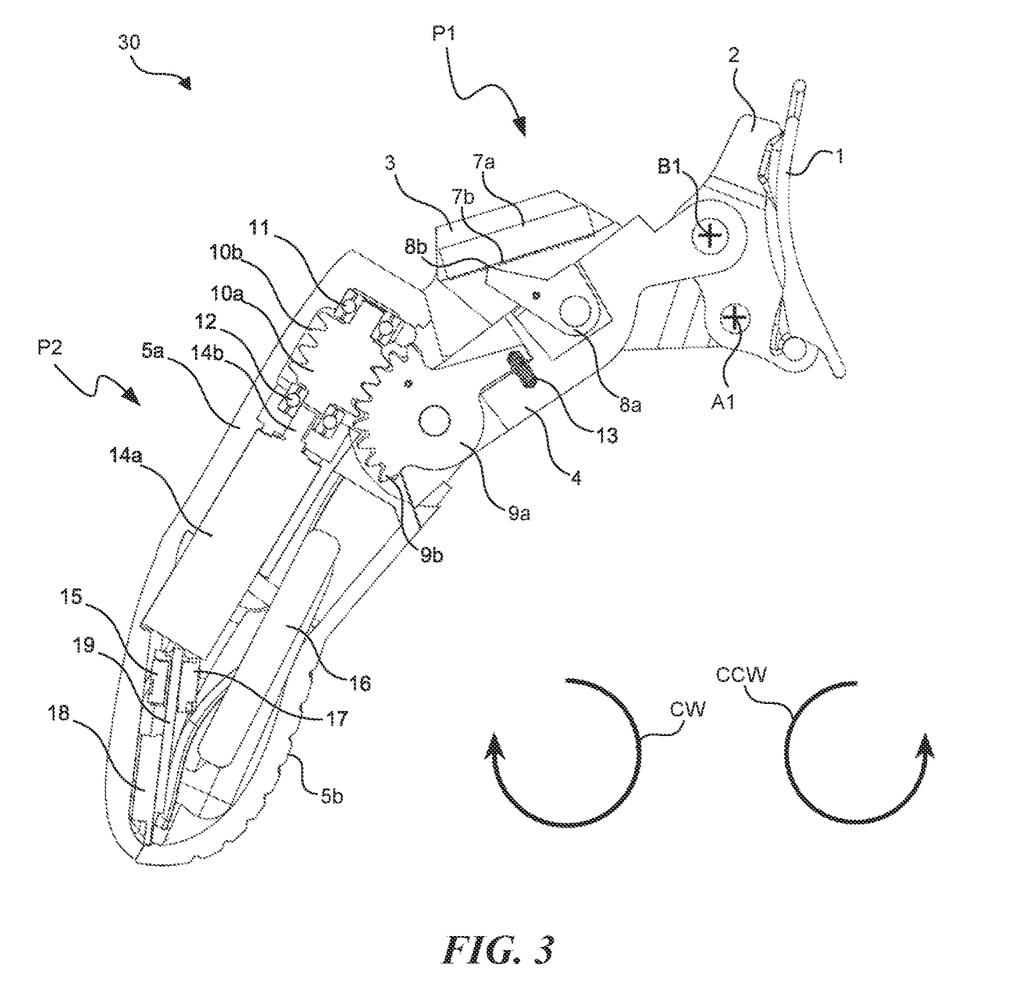
FIG. 3 shows a cross-sectional view of the powered prosthetic digit of FIGS. 1A and 1B.

FIG. 3 shows a cross-sectional view of the digit 30 further illustrating the internal configuration of the components therein. As best seen in FIG. 3, the first linkage 3 of the digit 30 may comprise a rack 7a having rack teeth 7b designed to engage a nose 8b of a pawl 8a such that free motion is allowed in a flexion direction (e.g., gripping movement), and a structural position lock is created in the extension direction, preventing the first and second segments P1 and P2 from rotating in the clockwise CW direction. The rack teeth 7b may be configured to interface with the nose 8b and may be fabricated of hardened steel or other sufficiently strong and wear-resistant material(s). The pawl 8a is connected in a rotationally pinned manner to the second linkage 4, and may be engaged/disengaged with the rack teeth 7b via a lock link 20 and a spring 13 acting on the positioning gear 9a, which will be explained in greater detail below with reference to FIGS. 4A and 4B. The posture required to achieve the hook grasp occurs when the nose 8b of the pawl 8a is engaged at an intermediate position on the rack 7a. When the digit 30 is loaded in the hook grasp position, the first and second linkages 3 and 4 have forces tending to place a compression load on the nose 8b of the pawl 8a, thereby maintaining the locked state, and avoiding loading the drivetrain components, e.g., the positioning gear 9a, the worm gear 10a, etc.

For example, during operation, the digit 30 can lock to oppose extension movement, allowing objects to be gripped and manipulated in a flexion position, against opposable digits, and/or in the palm of the hand. This "hook" type grasp position is utilized in various activities of daily living (ADLs), such as lifting a bucket of water by the handle or carrying a plastic grocery bag.

During operation of the digit 30 between the full extension and full flexion positions, rotation of the worm screw 10a via input from the motor 14a causes rotation about the positioning gear 9a, which causes rotation of the second segment P2 with respect to the first segment P1. The worm teeth 10b are configured to engage with the positioning teeth 9b to advance the angular position of the worm screw 10a with respect to the positioning gear 9a. The motor 14a is configured to operate in either rotational direction (clockwise/counterclockwise) to cause the digit 30 to either rotate toward full flexion or full extension depending upon the motion of the user. For example, when the user wants to grip an object, the motor 14a rotates the worm screw 10a in an appropriate direction (e.g., depending on the pitch of the worm teeth 10b) to cause angular rotation of the second segment P2 in the counterclockwise CCW direction with respect to the first segment P1 (as described above) and cause angular rotation of the first segment P1 in the counterclockwise direction CCW with respect to the base portion 2, and move the digit 30 in flexion and grip the object.

Figure 4A:
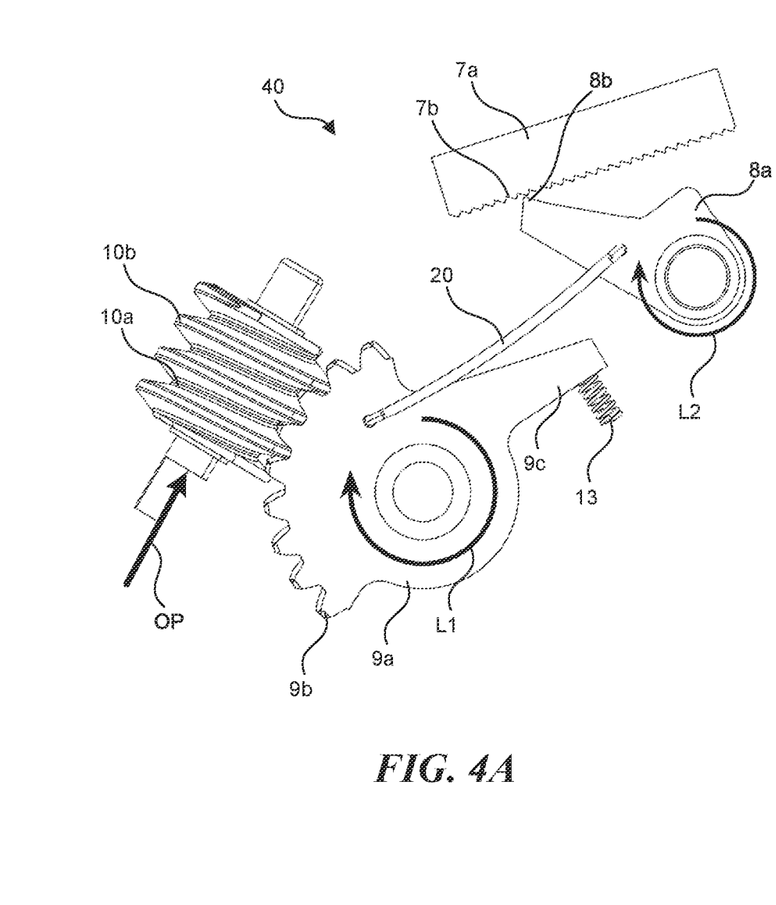
FIGS. 4A and 4B show a detailed view of the locking rack mechanism of the powered prosthetic digit of FIGS. 1A and 1B configured in accordance with an embodiment of the present technology.
Figure 4B:
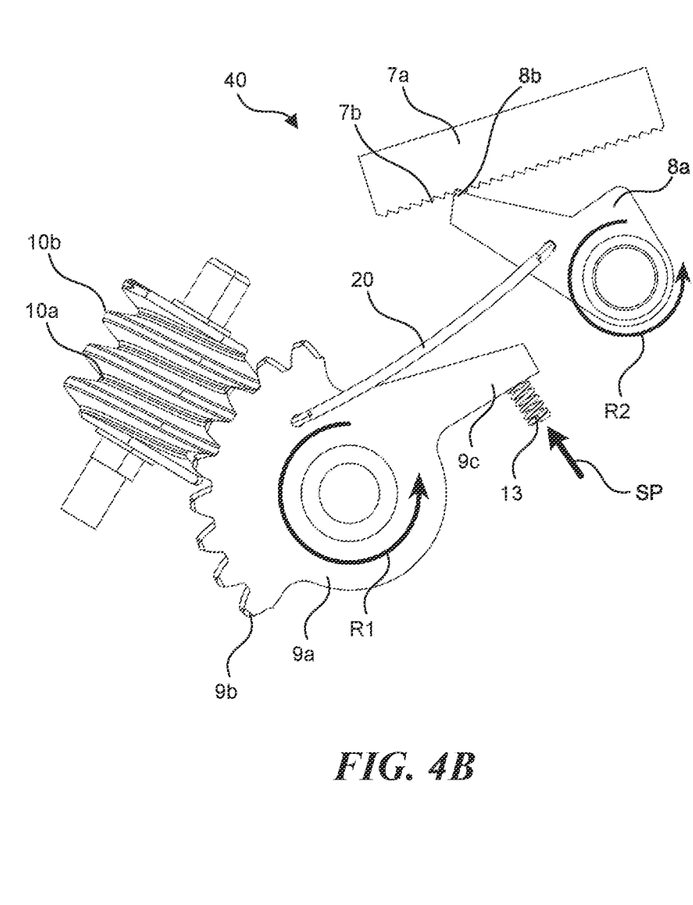
Figure 4C:
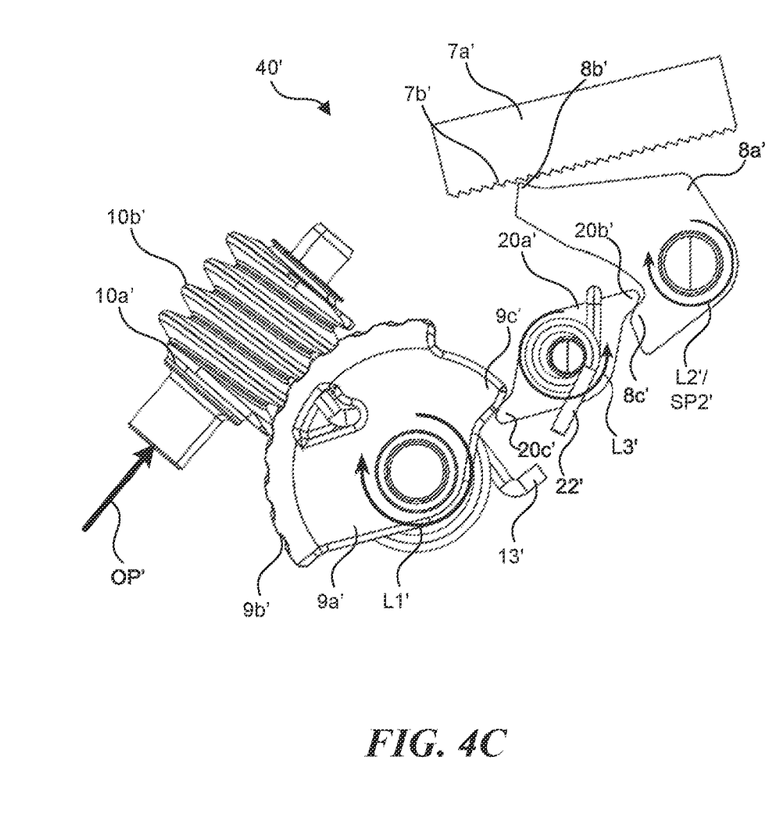
FIGS. 4C and 4D show a detailed view of the locking rack mechanism of the powered prosthetic digit of FIGS. 1A and 1B configured in accordance with another embodiment of the present technology.
Figure 4D:
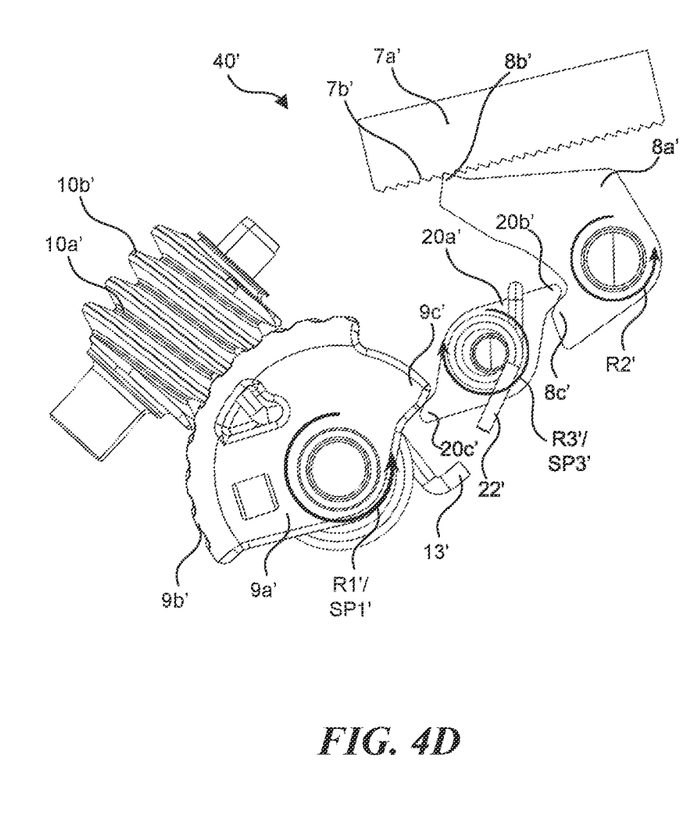

FIGS. 4A and 4B show detailed views of a locking rack mechanism 40 configured in accordance with embodiments of the present technology, and FIGS. 4C and 4D show detailed views of a locking rack mechanism 40' configured in accordance with further embodiments of the present technology. A number of components of the digit 30 (FIGS. 1A and 1B) are not shown in FIGS. 4A-4D for sake of clarity of illustration. As described above, during operation, the digit 30 can lock to oppose extension movement, allowing objects to be gripped and manipulated to hold objects in a flexion position, against opposable digits, and/or in the palm of the hand. The locking rack mechanisms 40 and 40' are shown in an unlocked position with the noses 8b and 8b' disengaged from the rack teeth 7b (FIG. 4A) and 7b' (FIG. 4C), respectively, and a locked position with the noses 8b and 8b' engaged with the rack teeth 7b (FIG. 4B) and 7b' (FIG. 4D), respectively. In the embodiment shown in FIGS. 4A and 4B, the lock link 20 rotationally couples the positioning gear 9a and the pawl 8a. In this regard, rotation of the positioning gear 9a will cause rotation of the pawl 8a in the same direction. In the embodiment shown in FIGS. 4C and 4D, a rocker arm 20a' rotationally couples the positioning gear 9a' and the pawl 8a' such that rotation of the positioning gear 9a' will cause rotation of the pawl 8a' in the same direction.

To lock the digit 30 for gripping an object, the pawls 8a and 8a' may be automatically engaged via a mechanism (e.g., a spring load mechanism) when the fingertip receives an opposition force (in the extension direction). During such automatic engagement, the noses 8b and 8b' engage respectively with the rack teeth 7b and 7b' in the racks 7a and 7a' and prevent extension. Removal of the opposition force on the digit 30 may automatically disengage the locking rack mechanisms 40 and 40', allowing the motor 14a (FIGS. 2 and 3) to move the digit 30 freely in either direction. In these embodiments, the drivetrain may comprise lightweight and relatively soft materials while the overall mechanism still has capability to oppose relatively high loads through the pawls 8a and 8a' and racks 7a and 7a'.

The automatic engagement and disengagement functionality of an embodiment of the locking rack mechanism 40 will now be described with reference to FIGS. 4A and 4B, and the locking rack mechanism 40' will be described with reference to FIGS. 4C and 4D. Referring initially to FIG. 4A, when the locking rack mechanism 40 is unlocked (as shown, with the nose 8b disengaged from the rack teeth 7b) and opposition force OP is applied through the drivetrain and the worm screw 10a, the engagement of the worm screw 10a with the positioning gear 9a causes rotation of the positioning gear 9a in a lock direction L1. Rotation of the positioning gear 9a in the lock direction L1 causes translation of the lock link 20 and corresponding rotation of the pawl 8a in a lock direction L2, engaging the nose 8b with the rack teeth 7b. As a result, the opposition force OP through the worm screw 10a locks the mechanism such that grip is retained on the object during use of the digit 30.

Referring now to FIG. 4B, when the digit 30 is locked (as shown, with the nose 8b engaged with the rack teeth 7b) and opposition force on the fingertip is released, the spring 13 applies a force SP into an arm 9c of the positioning gear 9a to cause rotation of the positioning gear 9a in a release direction R1. Rotation of the positioning gear 9a in the release direction R1 causes translation of the lock link 20 and corresponding rotation of the pawl 8a in a release direction R2, disengaging the nose 8b from the rack teeth 7b. In this regard, the force SP of the spring 13 unlocks the mechanism such that the motor 14a (FIGS. 2 and 3) can freely extend and flex the digit.

Referring next to FIG. 4C, when the digit 30 is unlocked (as shown, with the nose 8b' disengaged from the rack teeth 7b') and opposition force OP' is applied through the drivetrain and the worm screw 10a', the engagement of the worm screw 10a' with the positioning gear 9a' causes rotation of the positioning gear 9a' in a lock direction L1'. The positioning gear 9a' may include a protrusion 9c' in contact with a protrusion 20c' of the rocker arm 20a' such that rotation of the positioning gear 9a' in the lock direction L1' overcomes the spring forces of both the spring 13' of the positioning gear 9a' and the spring 22' of the rocker arm 20a', causing rotation of the rocker arm 20a' in the lock direction L3'. The corresponding rotation of the rocker arm protrusion 20b' releases pressure on the protrusion 8c' of the pawl 8a' and allows the pawl 8a' to rotate in a lock direction L2', engaging the nose 8b' with the rack teeth 7b'. The pawl 8a' may include a spring force SP2' in the lock direction L2' using a spring (not shown) or other suitable biasing member. As a result of this motion, the opposition force OP' acts through the worm screw 10a' and locks the mechanism such that grip is retained on the object during use of the digit 30.

Referring now to FIG. 4D, when the digit 30 is locked (as shown, with the nose 8b' engaged with the rack teeth 7b') and opposition force on the fingertip is released, the spring 13' applies a spring force SP1' to the positioning gear 9a' to cause rotation of the positioning gear 9a' in a release direction R1'. Rotation of the positioning gear 9a' in the release direction R1' allows a spring force SP3' to cause rotation of the rocker arm 20a' in the release direction R3' and corresponding rotation of the pawl 8a' in a release direction R2' by contact of the protrusion 20b' with the protrusion 8c', disengaging the nose 8b' from the rack teeth 7b'. In this regard, the spring forces SP1 ' and SP3' unlock the mechanism such that the motor 14a (FIGS. 2 and 3) can freely extend and flex the digit 30.

Figure 5:
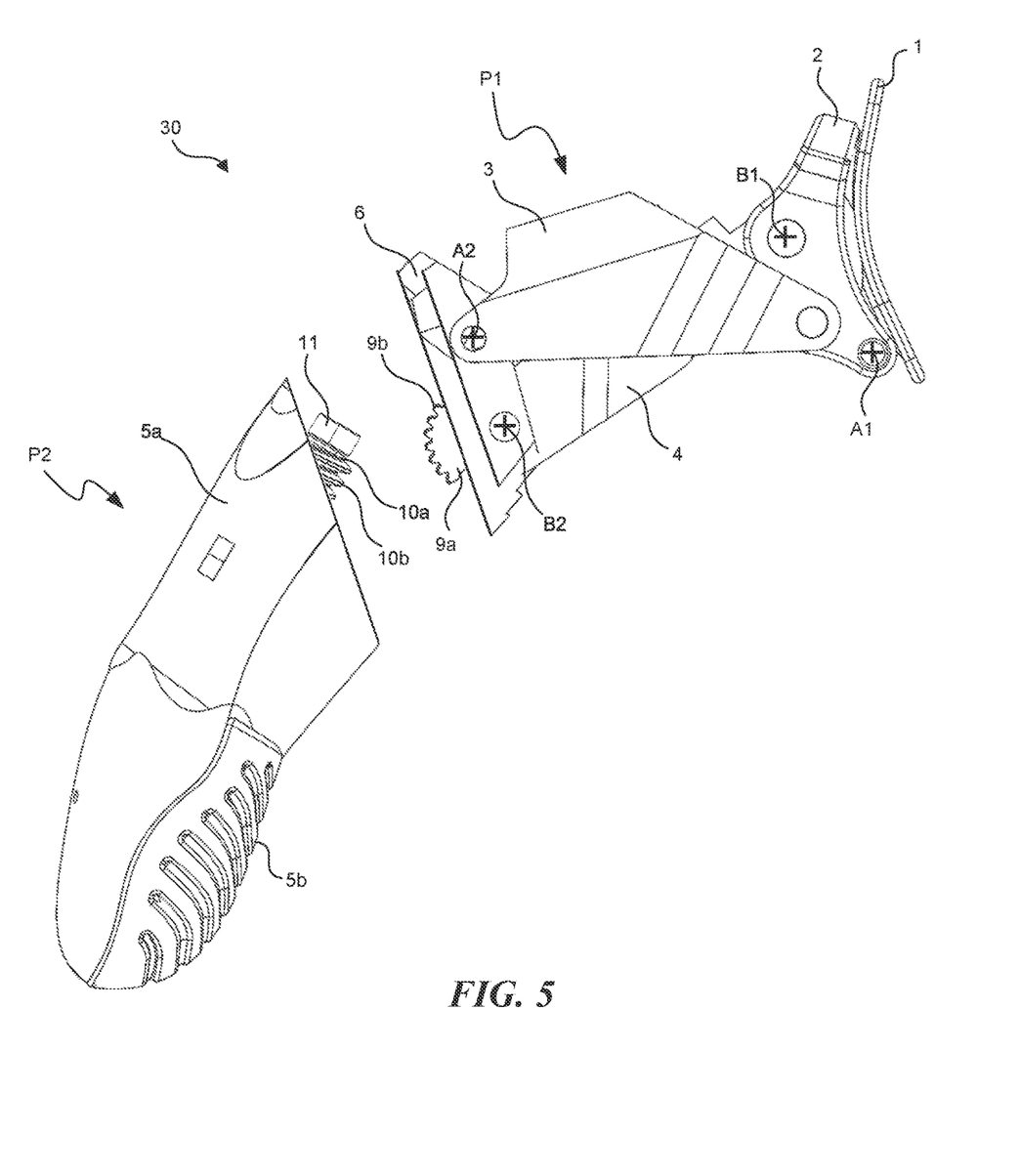
FIG. 5 shows a partially disassembled view of the powered prosthetic digit of FIGS. 1A and 1B.

FIG. 5 shows a partially disassembled view of the digit 30 where the second segment P2 is separated from the first segment P1 for access during replacement and charging. For example, a user may carry one or more backup second segments P2 to replace a second segment P2 that has malfunctioned or lost sufficient battery charge to be operational. As shown, the grip fairing 5a and the internal components therein may be separated from the connector plate 6 to separate the first and second segments P1 and P2. It will be further appreciated that other separation states are also within the scope of the present technology.

Figure 6A:
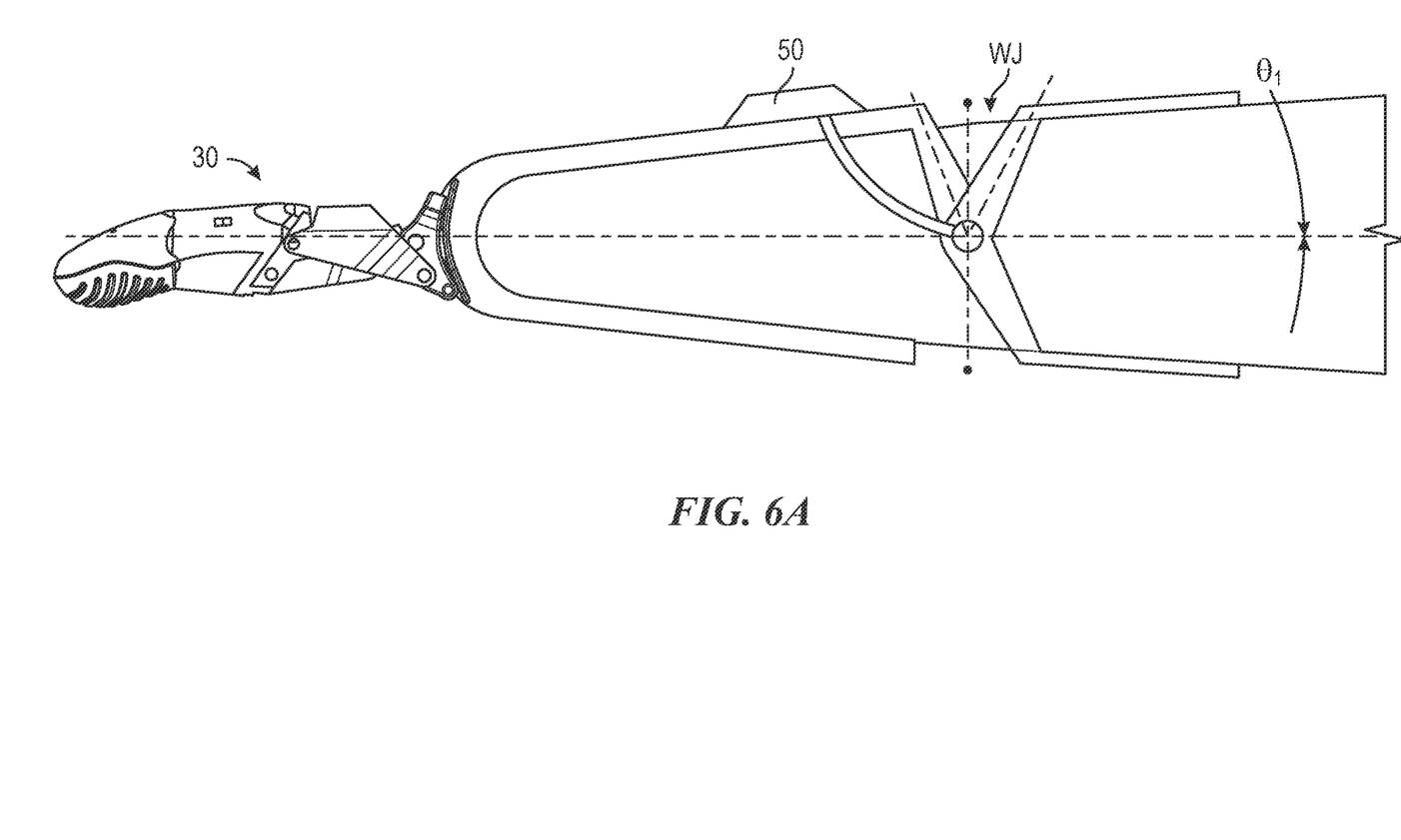
FIGS. 6A and 6B show one configuration of attaching the powered prosthetic digit of FIGS. 1A and 1B to a user in accordance with embodiments of the present technology.
Figure 6B:
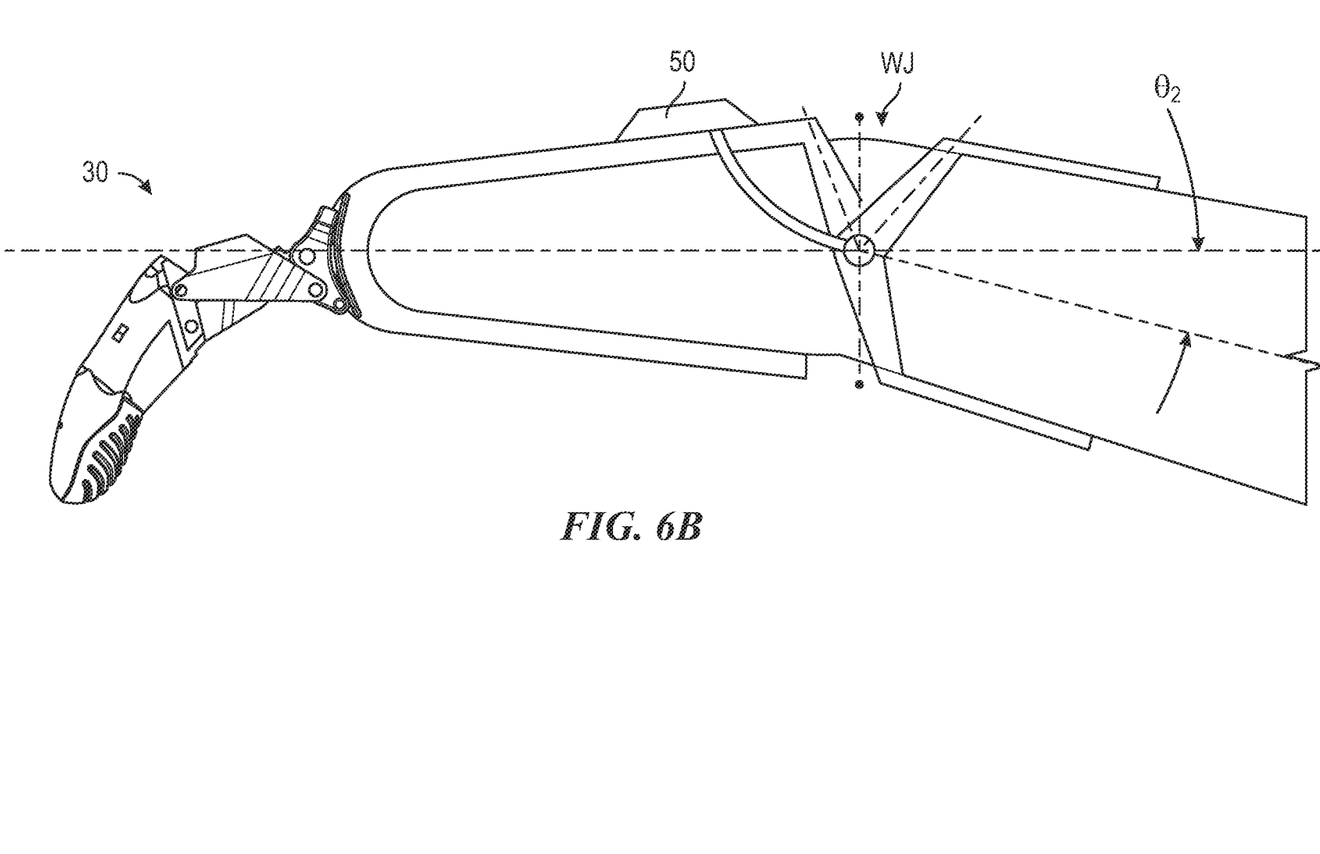

FIGS. 6A and 6B show one configuration of attaching the digit 30 to a user in accordance with embodiments of the present technology. In particular, FIG. 6A shows the digit 30 in an extended position, while FIG. 6B shows the digit 30 in an intermediate flexion position. The digit 30 is capable of freedom of motion in the radial-ulnar deviation (RUD) directions. Allowing for a degree of freedom in the RUD directions preserves the function of the wrist in positioning the hand in space and provides an additional control input. In the illustrated embodiment in FIGS. 6A and 6B, the digit is controlled with wireless signals via wrist motion. As such, a sensor 50 may be applied across the wrist joint WJ to capture posture in both flexion/extension and radial/ulnar deviation (RUD). The posture creates angular data signals in the sensor 50 that are transmitted to the digit 30 and used to control individual digit posture (e.g., the extended position shown in FIG. 6A where angle $\theta_1$ is about 0°, the intermediate flexion position shown in FIG. 6B where angle $\theta_2$ is about 15°, or any other suitable position within the range of the wrist joint WJ) and/or velocity of the digit 30, or relative digit posture and/or velocity when multiple prosthetic digits 30 are in use.

In some embodiments, the digit 30 may have one or more of the following specifications: (1) low-force motor with an active force capability at fingertip of less than 2 N; (2) high speed motor with 140-360 deg/sec motion capability (MCP joint velocity during gesticulation can be ~166 deg/sec); (3) pinch force opposition capability greater than 133 N; (4) hook grasp force capability greater than 155 N; (5) field removable finger; (6) water resistant, fully potted electronics; (7) battery embedded in contained finger; and (8) coupled to wrist motion, controlled via wireless or wired communication. In some embodiments, the digit 30 may be configured to move in reaction to wrist posture measurements.

C. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments.

For ease of reference, identical reference numbers are used to identify similar or analogous components or features throughout this disclosure, but use of the same reference number does not imply that the features should be construed to be identical. Indeed, in some examples described herein, identically numbered features may have a plurality of embodiments that are distinct in structure and/or function from each other. Furthermore, the same shading may be used to indicate materials in cross section that can be compositionally similar, but shading type does not imply that the materials should be construed to be identical unless specifically noted herein.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A prosthetic distal segment couplable to a proximal segment of a prosthetic digit that is pivotably coupled to a base, the prosthetic distal segment comprising:
    a fairing;
    a motor positioned within the fairing;
    a drive gear rotationally coupled to the motor and operable to pivot the proximal segment with respect to the base; and
    a battery positioned within the fairing and electrically coupled to the motor.

2. The prosthetic distal segment of claim 1, wherein, when the prosthetic distal segment is coupled to the proximal segment of the prosthetic digit, the prosthetic digit is configured to resist a force greater than 222 N applied to the prosthetic digit in a direction that causes extension of the prosthetic digit.

3. The prosthetic distal segment of claim 1, wherein the prosthetic distal segment is configured to be removably couplable to the proximal segment of the prosthetic digit.

4. The prosthetic distal segment of claim 3, wherein the fairing further comprises an external grip portion, and wherein the distal segment is removably couplable to a connector plate of the proximal segment.

5. The prosthetic distal segment of claim 1, wherein the proximal segment is a four-bar linkage including a connector plate removably coupled to the distal segment, and wherein the four-bar linkage is configured to rotate the connector plate at a greater angular velocity with respect to the base than an angular velocity of the proximal segment with respect to the base during articulation of the prosthetic digit.

6. The prosthetic distal segment of claim 1, wherein the drive gear is a worm screw, and wherein rotation of the worm screw causes a change in engagement position along a positioning gear of the proximal segment.

7. The prosthetic distal segment of claim 1, further comprising an electronics control board positioned within the fairing, wherein the electronics control board comprises a microprocessor electronically coupled to the motor and configured to control the motor in response to one or more of a signal, algorithm, function, and command.

8. The prosthetic distal segment of claim 7, wherein the battery is electrically coupled to the electronics control board and configured to power the motor.

9. The prosthetic distal segment of claim 1, wherein the motor is configured to pivotably rotate the proximal segment with respect to the base at an angular velocity of at least 140 deg/sec.

10. The prosthetic distal segment of claim 1, wherein the motor is configured to apply a grasping force through the prosthetic digit of less than 2 N.

11. A prosthetic digit, comprising:
a proximal segment pivotably coupled to a base;
a prosthetic distal segment coupled to the proximal segment, wherein the prosthetic distal segment includes—
  a fairing;
  a motor positioned within the fairing;
  a drive gear rotationally coupled to the motor and operable to pivot the proximal segment with respect to the base; and
  a battery positioned within the fairing and electrically coupled to the motor; and
a positioning gear pivotably coupled to the proximal segment, wherein the positioning gear is configured to operatively engage with the drive gear to pivot the proximal segment with respect to the base.

12. The prosthetic digit of claim 11, wherein the prosthetic digit is configured to resist a force greater than 222 N applied to the prosthetic digit in a direction that causes extension of the prosthetic digit.

13. The prosthetic digit of claim 11, wherein the prosthetic digit is configured to output a grasping power of less than 200 mW at a distal end of the prosthetic distal segment.

14. The prosthetic digit of claim 11, wherein the proximal segment further comprises a first linkage with a proximal end pivotably coupled to the base and a second linkage with a proximal end pivotably coupled to the base and extending in a crossed configuration with the first linkage, wherein the first linkage comprises a rack.

15. The prosthetic digit of claim 14, further comprising a connector plate pivotably coupled to a distal end of the first linkage and a distal end of the second linkage, wherein the connector plate, the first linkage, the second linkage, and the base form a four-bar linkage configuration.

16. The prosthetic digit of claim 11, wherein the proximal segment further comprises a rack with a plurality of rack teeth and a pawl with a nose configured to engage with the rack to prevent pivoting of the proximal segment in a rotational direction corresponding to extension of the prosthetic digit.

17. The prosthetic digit of claim 16, wherein:
the proximal segment further comprises a lock link coupled between the positioning gear and the pawl,
the lock link is operable to rotate the pawl upon rotation of the positioning gear, and
the rotation of the positioning gear causes the pawl to transition between a locked state, in which the nose is engaged with the rack teeth, and an unlocked state, in which the nose is disengaged from the rack teeth.

18. The prosthetic digit of claim 16, wherein:
the proximal segment further comprises a rocker arm positioned between the positioning gear and the pawl,
the rocker arm is operable to allow rotation of the pawl upon rotation of the rocker arm, and
the rotation of the rocker arm causes the pawl to transition between a locked state, in which the nose is engaged with the rack teeth, and an unlocked state, in which the nose is disengaged from the rack teeth.

19. A prosthetic digit, comprising:
a proximal segment pivotably coupled to a base, wherein the proximal segment includes—
  a rack with a plurality of rack teeth; and
  a pawl with a nose configured to engage with the rack to prevent pivoting of the proximal segment in a rotational direction corresponding to extension of the prosthetic digit;
a prosthetic distal segment coupled to the proximal segment, wherein the prosthetic distal segment includes—
  a fairing;
  a motor positioned within the fairing;
  a drive gear rotationally coupled to the motor and operable to pivot the proximal segment with respect to the base; and
  a battery positioned within the fairing and electrically coupled to the motor; and
a positioning gear pivotably coupled to the proximal segment, wherein the positioning gear is configured to operatively engage with the drive gear to pivot the proximal segment with respect to the base,
wherein rotation of the positioning gear causes the pawl to transition between a locked state, in which the nose is engaged with the rack teeth, and an unlocked state, in which the nose is disengaged from the rack teeth.

20. The prosthetic digit of claim 19, further comprising a spring coupled between the proximal segment and the positioning gear, wherein the spring is configured to bias the pawl towards the unlocked state.

* * * * *